United States Patent [19]
Roth

[11] Patent Number: 5,080,108
[45] Date of Patent: Jan. 14, 1992

[54] SURGICAL DRAPE

[76] Inventor: Robert A. Roth, 1636 St. Mary's La., Festus, Mo. 63028

[21] Appl. No.: 505,500

[22] Filed: Apr. 6, 1990

[51] Int. Cl.$^5$ ............................................. A61F 13/00
[52] U.S. Cl. ..................................... 128/849; 128/852
[58] Field of Search ................................. 128/849–856; 604/174, 179, 180

[56] References Cited

U.S. PATENT DOCUMENTS

| | | | |
|---|---|---|---|
| 4,067,327 | 1/1978 | Shannon, Sr. | 128/849 |
| 4,342,392 | 8/1982 | Cox | 206/438 |
| 4,671,787 | 6/1987 | Widman | 604/179 |
| 4,804,367 | 2/1989 | Smith et al. | 604/113 |
| 4,869,271 | 9/1989 | Idris | 128/853 |
| 4,887,615 | 12/1989 | Taylor | 128/850 |
| 4,889,136 | 12/1989 | Hanssen | 128/855 |
| 4,905,710 | 3/1990 | Jones | 128/849 |
| 4,941,479 | 7/1990 | Russell et al. | 128/855 X |

Primary Examiner—Mickey Yu
Assistant Examiner—Kerry Owens
Attorney, Agent, or Firm—Polster, Lieder, Woodruff & Lucchesi

[57] ABSTRACT

A sterile surgical drape sufficiently wide to circumferentially cover and enclose a non-sterile element such as tubing and a junction between the non-sterile element and a sterile element includes a malleable strip adhered to the inside of the drape, the strip being bent around the non-sterile element that the drape covers. The malleable strip maintains the drape around the non-sterile element so that it will not contaminate a sterile field. The drape may be adhered to a sterile field by means of adhesive strips on the outside of the drape. The drape includes adhesive strips along its side to hold the drape closed about the non-sterile element. The drape may also include a pair of holes so that it may be hung from an IV pole to enclose the IV pole.

5 Claims, 1 Drawing Sheet

SURGICAL DRAPE

BACKGROUND OF THE INVENTION

This invention relates to sterile surgical drapes, and, in particular, to a sterile surgical drape that may be conformed to a shape of surgical tubing, cables, devices or an I.V. pole, or other non-sterile object to cover the the non-sterile object and preserve the sterility of the operative field.

Many medical procedures are performed under sterile conditions. These procedures often require that I.V. bottles and tubing, or devices and their components, including wires, be hung from I.V. poles and connected in some way with the patient. The tubing, devices and the cables connected to the devices, instruments or consoles are normally non-sterile and are often connected to a sterile counterpart which leads to the patient.

Accidental contact by the operating room personnel or the patient with the non-sterile elements would violate the sterile integrity of the procedure and risk contamination of the sterile area and infection to the patient.

SUMMARY OF THE INVENTION

One object of the present invention is to provide a sterile surgical drape which may isolate non-sterile components in an operating room from the sterile field.

Another object of the present invention is the provision of such a surgical drape which is relatively simple and inexpensive in construction.

A third object is the provision of such a surgical drape which readily conforms to the shape of the non-sterile element being covered and remains in place about said element.

Other objects will become apparent to those skilled in the art in light of the following disclosure and accompanying drawings.

Briefly, a sterile surgical drape of the present may be circumferentially wrapped around non-sterile components, such as an I.V. pole, I.V. tubing, cables or the like, in an operating room to isolate the non-sterile elements from a sterile field, so that the sterile field will not be contaminated by accidental contact with the non-sterile elements by operating room personnel. The drape includes a generally flat piece of sterile material having an inside, an outside, and top, bottom, and side edges. Malleable strips are disposed in the middle of the top of the drape so that the drape may be formed around the non-sterile element to be isolated. The malleable strips are preferably a pair of parallel, spaced apart, aluminum strips. Adhesive strips are placed along the side edges of the drape to hold the drape closed around the non-sterile element. The adhesive strips are preferably covered prior to use.

In the preferred embodiment, there is a preformed crease down the middle of the drape. When the drape is folded over, the crease causes the side edges to align more easily, making closure of the drape easier.

A window may be placed through the drape around the malleable strips. This allows operating room personnel to visually observe the component about which the drape is folded during the procedure.

The drape is preferably water resistant to keep contaminants from flowing from the inside to the sterile outside of the drape, which could compromise the integrity of the sterile field.

The drape may further include adhesive strips on the outside thereof, so that the drape may be secured to the sterile field. There are preferably two adhesive strips, one on either side of the crease, so that the orientation of the drape will not interfere with the ease of securing it to the sterile field.

The drape may also include a pair of holes at its bottom which support the drape on cross bars of an I.V. pole.

BRIEF DESCRIPTION OF THE DRAWINGS

Similar reference characters indicate similar parts throughout the several views of the drawings.

DESCRIPTION OF THE PREFERRED EMBODIMENT

Figure 1:
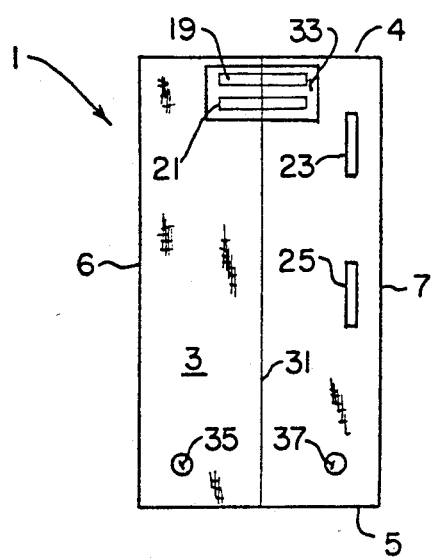
FIG. 1 is a plan view of the sterile surgical drape of the present invention.
Figure 2:
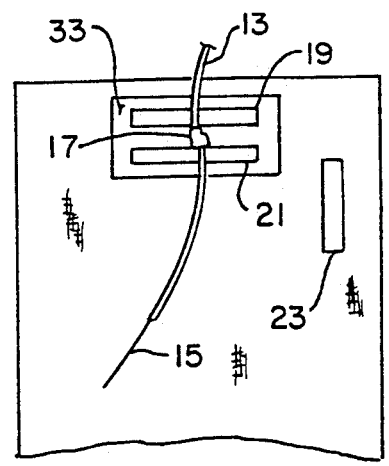
FIG. 2 shows a junction between sterile and non-sterile tubing on the drape of FIG. 1.
Figure 3:
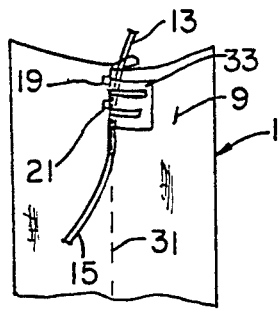
FIGS. 3 and 4 illustrate folding and closing the drape about the tubing of FIG. 2.
Figure 4:
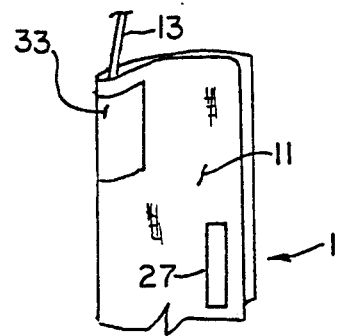

Referring to the FIGURES, a sterile surgical drape 1 of the present invention includes a generally flat piece of sterile or sterilizable material 3 having a top 4, a bottom 5, and two sides 6 and 7. That portion of drape 1 shown in FIG. 1 is referred to as the inside of the drape while the outside, labelled 11, is partially shown in FIG. 4.

Drape 1 may be circumferentially folded about non-sterile tubing 15 to isolate the non-sterile tubing from a sterile field so that the non-sterile tubing will not contaminate or otherwise violate the sterile integrity of an ongoing sterile procedure.

The non-sterile element 15 may come from an I.V. bottle, instrument or a surgical device (not shown) and is typically connected to a sterile counterpart 13 at a junction 17, the sterile counterpart being suitably connected to the patient.

Because the drape 1 covers non-sterile element 15, its inside upon exposure to the non-sterile element can no longer be considered sterile. The outside 11, however, maintains its sterility. To ensure this, the drape is preferably water resistant. If the outside of the drape should get wet and the drape were not water resistant, liquid would soak through to the inside, and contaminants could flow from the inside to the outside. Thus, to avoid contamination of the sterile area due to liquid on the drape, the drape is preferably made water resistant. This may be in the form of a water resistant lamination which is applied to standard surgical drape material.

Drape 1 includes a pair of malleable aluminum strips 19, 21 and a pair of adhesive strips 23, 25 on its inside 9. An outer adhesive strip 27 (FIG. 4) is placed on the outside 11 of drape 1 so that the drape may be secured to the sterile field. There may be two adhesive strips 27 mounted on opposite sides of outside 11 so the drape 1 may be easily secured to the sterile field independently of its orientation. Adhesive strips 23, 25, and 27 are initially covered with peel-off covers which are removed to expose the adhesive strip when needed.

Malleable strips 19, 21 are preferably laminated aluminum strips such as those sold under the commercial name of Flex-Form. Strips 19, 21 are located in the middle and at the top of drape 1 in a parallel spaced relationship.

In use, non-sterile element 15 and sterile element 13 are joined between strips 19 and 21. Placing junction 17 between the two strips aids in maintaining the tubes together, especially when they are of different diameters. With adhesive strips 23, 25 exposed, drape 1 is folded in half around the tubes by bending strips 19 and 21. The edges of the drape are then held together by adhesive strips 23 and 25. Adhesive strip 23 is preferably near the top of drape 1 to keep the drape from gapping or flapping open when it is folded over. There is preferably a preformed crease 31 down the center of drape 1 so that when the drape is folded over, the edges will meet. Crease 31 bisects strips 19 and 21.

Drape 1 may optionally have a window 33 behind malleable strips 19 and 21, so that the junction 17 between non-sterile element 15 and sterile element 13 is visible. This allows the operating room personnel to visually observe the condition of junction 17. Window 33 may contain adhesive material to further secure connection of junction 17.

Figure 5:
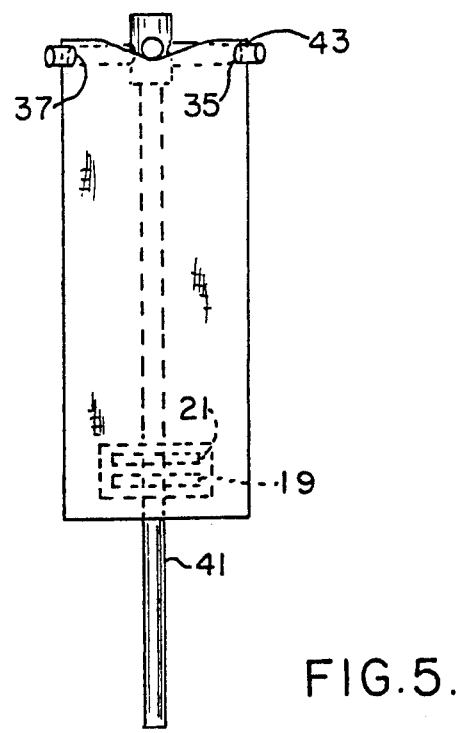
FIG. 5 shows the drape mounted on an I.V. pole.

Drape 1 may also define a pair of holes 35 and 37 at the bottom thereof. Holes 35 and 37 aid in supporting drape 1 on an I.V. pole 41 (FIG. 5) having cross bars 43 at its top which support I.V. bottles and other devices. It should be appreciated that when used in connection with an IV pole, malleable strips 19 and 21 may also be formed around cable, tubing or the pole itself as desired.

Numerous variations within the scope of the appended claims will be apparent to those skilled in the art in light of the foregoing description and accompanying drawings. For example, adhesive strips 23 and 25 may be replaced with hook and pile fasteners, with one portion of the fastener on one side edge and its counter part on the opposite edge. This variation is merely illustrative.

I claim:

1. A sterile surgical drape mounted upon a non-sterile IV pole having crossbars at the top thereof and about non-sterile devices, tubing, wires, cables, and the like which depend from said IV pole; said drape comprising a generally flat piece of sterile material having a top, bottom and side edges; said flat piece of sterile material having a length from top to bottom substantially greater than its width from side to side, a pair of apertures through said piece of sterile material, said apertures being disposed generally on opposite sides of the piece of sterile material and generally adjacent the top of the piece of sterile material, said apertures cooperating with said crossbars to support said drape from said crossbars so that substantially the entire length of the piece of sterile material extends downwardly from the crossbars; and closure means along the sides of the drape for maintaining said drape closed around said associated devices, wires, cables, tubing, and the like.

2. The sterile drape of claim 1, wherein said drape further includes malleable means for conforming said drape to the shape of said associated devices and for holding the drape in place about said associated devices.

3. The sterile drape of claim 2, wherein said malleable means comprises at least one malleable strip midway between said edges of said drape and at the opposite end of the drape from said apertures.

4. The sterile drape of claim 3, further including a transparent window through the drape at the location of the malleable strip so that said malleable strip is visible.

5. The sterile drape of claim 1, wherein said drape is liquid resistant.

* * * * *